United States Patent [19]

Vernaleken et al.

[11] 3,959,335

[45] May 25, 1976

[54] PROCESS FOR THE PREPARATION OF A BISPHENOL BISCHLOROCARBONIC ACID ESTER

[75] Inventors: Hugo Vernaleken; Kurt Weirauch; Günther Lenz, all of Krefeld; Uwe Hucks, Duisburg, all of Germany

[73] Assignee: Bayer Aktiengesellschaft, Leverkusen, Germany

[22] Filed: Mar. 4, 1975

[21] Appl. No.: 555,149

[30] Foreign Application Priority Data

Mar. 6, 1974 Germany............................ 2410743

[52] U.S. Cl. .............................................. 260/463
[51] Int. Cl.² .................... C07C 68/00; C07C 69/96
[58] Field of Search ...................................... 260/463

[56] References Cited
UNITED STATES PATENTS

| | | | |
|---|---|---|---|
| 3,170,946 | 2/1965 | Kilsheimer et al................. | 260/463 |
| 3,189,640 | 6/1965 | Dietrich et al...................... | 260/463 |
| 3,211,775 | 10/1965 | Stephens et al..................... | 260/463 |
| 3,275,674 | 9/1966 | Bottenbruch et al............... | 260/463 |
| 3,312,661 | 4/1967 | Kurkjy et al....................... | 260/463 X |
| 3,312,662 | 4/1967 | Kurkjy et al....................... | 260/463 X |

FOREIGN PATENTS OR APPLICATIONS 878,115   9/1961   United Kingdom................. 260/463

*Primary Examiner*—Joseph Paul Brust
*Attorney, Agent, or Firm*—Connolly and Hutz

[57] ABSTRACT

A continuous process for the production of a bisphenol bischlorocarbonic acid ester wherein an aqueous solution of a dialkali metal salt of a hydroquinone or a bisphenol is reacted in a pump circulating system with 2.5 to 5.0 mol, per mol of dihydroxy compound of phosgene dissolved in a suitable solvent for the bischlorocarbonic acid ester formed in the reaction under the addition of an alkali metal hydroxide solution to keep the pH-value between 9.0 and 12.0, the organic phase obtained is separated wherefrom the bisphenol bischlorocarbonic acid ester is isolated by distillation and/or crystallisation.

6 Claims, 1 Drawing Figure

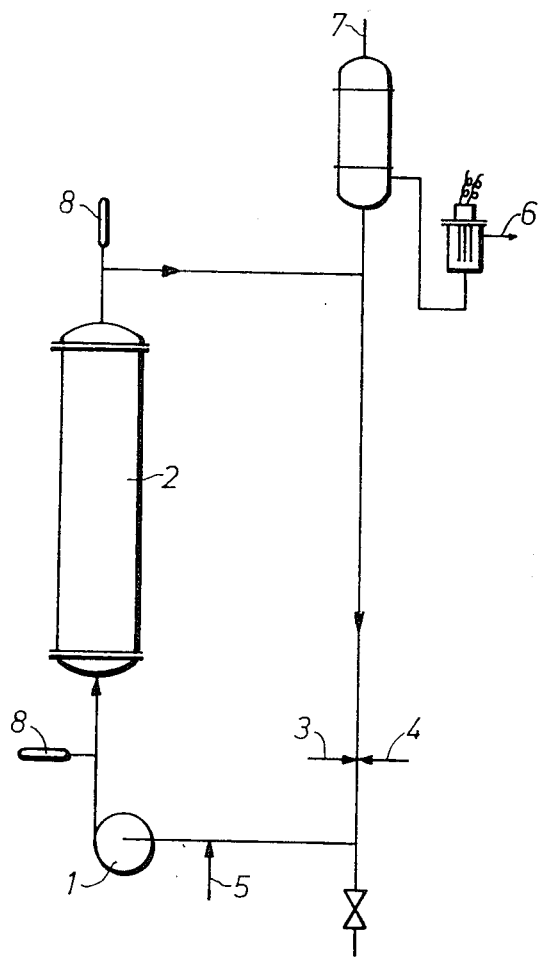

PROCESS FOR THE PREPARATION OF A BISPHENOL BISCHLOROCARBONIC ACID ESTER

This invention relates to a continuous process for the preparation of a bischlorocarbonic acid ester of an aromatic dihydroxy compound.

Usually bisphenol bischlorocarbonic acid esters are prepared by reacting aromatic dihydroxy compounds with excess phosgene in the presence of tertiary amines. This method is dangerous because the total quantity of phosgene required must be placed into the reaction vessel and, in many cases, phosgene and the tertiary amine together form resinous complexes which are only slightly soluble at low temperatures and react only at higher temperatures, sometimes vigorously and in an uncontrolled manner. The reaction mixtures are difficult and expensive to process since the tertiary amines must be separated in the form of the aqueous solutions of their hydrochlorides and regenerated with alkali.

An alternative method comprises reacting a bisphenol with excess phosgene in the presence of a nitrogen compound such as an acid amide, nitrile or quaternary ammonium salt as catalyst. Here again, the total quantity of phosgene must be placed into the reaction vessel and the reaction temperature must be high enough to cause the phosgene to boil in order to obtain a sufficiently high reaction velocity.

Since hydrogen chloride is split off at the same time, recycling of the phosgene from the gaseous phase by an efficient cooling system is difficult. The process also involves corrosion problems which are hard to overcome.

These dangers and difficulties are obviated by the present invention which relates to a continuous process for the production of a bisphenol bischlorocarbonic acid ester wherein an aqueous solution of a dialkali metal salt of a hydroquinone or of an aromatic dihydroxy compound of the general formula I

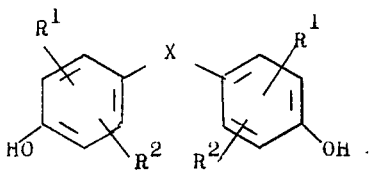

I in which X represents an alkylene or alkylidene with 1 to 6 carbon atoms, cycloalkylene or cycloalkylidene with 5 to 15 carbon atoms, O, S, $SO_2$ or

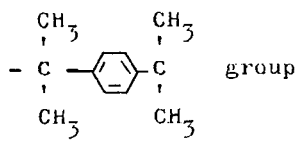

group and $R^1$ and $R^2$, which may be the same or different, represent an alkyl group with 1 to 4 carbon atoms or chlorine or bromine atom, is reacted in a pump circulating system with 2.5 to 5.0 mol, per mol of dihydroxy compound of phosgene dissolved in a suitable solvent for the bischlorocarbonic acid ester formed in the reaction under the addition of an alkali metal hydroxide solution to keep the pH-value between 9.0 and 12.0, the organic phase obtained is separated wherefrom the bisphenol bischlorocarbonic acid ester is isolated by distillation and/or crystallisation.

Bisphenols which react with alkali metal hydroxides such as lithium hydroxide, sodium hydroxide or potassium hydroxide in dilute aqueous solutions to form soluble alkali metal salts with concentrations of 5 to 30 % by weight in the aqueous solution are suitable for the process according to the invention. The mentioned alkali metal hydroxide solutions themselves are also used in the inventive process.

The following are examples of such bisphenols: dihydroxy diaryl alkanes such as bis-(4-hydroxyphenyl)-propane-2,2 (bisphenol A), bis-(3,5-dichloro-4-hydroxyphenyl)-propane-2,2 (tetrachlorobisphenol A), bis-(3,5-dibromo-4-hydroxyphenyl)-propane-2,2(tetrabromobisphenol A), bis-(3,5-dimethyl-4-hydroxyphenyl)-propane-2,2 (tetramethyl bisphenol A), bis-(4-hydroxyphenyl)-cyclohexane-1,1 (bisphenol Z),$\alpha\alpha'$-bis-(4-hydroxyphenyl)-diisopropyl benzene (trinuclear bisphenol), hydroquinone, bis-(4-hydroxyphenyl)-sulphide, bis-(4-hydroxyphenyl)- sulphone and bis-(4-hydroxyphenyl)-ether. The substances specifically mentioned are preferred.

Suitable solvents for the bischlorocarbonic acid ester formed and thus for the phosgene include aromatic hydrocarbons such as benzene, toluene and xylene and clorinated hydrocarbons such as methylene chloride, chloroform carbon tetrachloride and 1,2-chlorodiethane and chlorobenzene and the chlorotoluenes.

Moreover, any solvents which are immiscible with water and capable of dissolving the bischlorocarbonic acid esters formed in the reaction may be used.

Continuous reactors which ensure vigorous mixing of the reaction components and a high flow velocity are suitable for carrying out the reaction of the aqueous alkali metal salt solution of the bisphenols with phosgene. Reynolds numbers of at least 2000 are required for obtaining high conversion rates and yields.

The accompanying diagram shows a circulating pump reactor of the type preferably used in the process according to the invention which comprises a delivery pump 1, a circulating cooler 2 for removing the heat of reaction, a feed pipe for the aqueous alkali metal salt solution of the bisphenols 3 and for the additional alkali metal hydroxide solution 5 and the phosgene solvent mixture 4. A suitable measuring instrument for controlling the pH is installed in the overflow of the reactor 6 and temperature measuring points 8 are provided before and after the reactor. A ventilator 7 is also installed in the system.

The alkali metal salt solution of the dihydroxy diaryl alkanes together with the phosgene dissolved in solvent is introduced first into the reaction system at a point upstream of the delivery pump (e.g. a rotary pump) and the alkali metal hydroxide solution is then introduced after an interval of at least 1 second.

The quantity of phosgene required for preparing the bischlorocarbonic acid ester is 2.5 to 5.0 mol per mol of dihydroxy compound. 3.5 to 4.0 mol of phosgene per mol of dihydroxy compound are preferably used. Maximum yields are obtained when these proportions are used and the pH is kept between 9.0 and 12.0 by adding alkali metal hydroxide solution as required. The quantity of alkali metal hydroxide solution used is adjusted to the quantity of phosgene.

The optimum pH of the reaction mixture with respect to the yield and phosgene consumption is correlated with the $p_K$-value of the dihydroxy compound: thus for example the optimum pH shifts to lower values when less basic dihydroxy compounds are used (tetrachlorobisphenol A), in which case it is in the region of about 9.5, whereas the bisphenol A the optimum pH is in the region of about 10.5.

The reaction mixtures should stay less than 12 minutes in the reactor. If longer reaction times are employed, which is in principle quite possible and may be desirable in the case of sterically strongly hindered dihydroxy compounds, the yields are reduced. The extent to which the dwelling time can be reduced is limited by the apparatus itself, for example the construction of the reactor and/or by the removal of the reaction enthalpy. It may be assumed that the lower limit is in the region of about 2 minutes.

The reaction temperatures are generally 0° to 50°C. The reaction is preferably carried out from 0° to 25°C. Optimum results with regard to phosgene consumption and yield are obtained with volume/time yields of between 0.5 and 2.0 kg of bischlorocarbonic acid ester per liter of reaction volume and hour.

The bischlorocarbonic acid ester formed in the reaction is isolated from the reaction mixture after separation of the aqueous reaction phase, which can easily be carried out in a very short time (less than 5 minutes) by known methods in known apparatus such as separating vessels or centrifuges. It can be achieved, for example, by crystallisation by cooling, optionally after distilling off some of the solvent, or by evaporation of the solvent and distillation of the residue.

Very pure bischlorocarbonic acid esters are obtained if before the bischlorocarbonic acid ester is isolated, the organic reaction phase is washed free from electrolytes with water. This is also may suitably be carried out with known systems such as mixers/separators or washing centrifuges.

The yields obtained by the process according to the invention are between 75 and 95% of the theory, based on the quantity of dihydroxy compounds used. The conversion of dihydroxy compounds is almost quantitative.

Bisphenol bischlorocarbonic acid esters are valuable intermediate products for the synthesis of polycarbonates and polyurethanes.

EXAMPLE 1 a. Bisphenol A-bischlorocarbonic acid ester 60.8 kg of an aqueous disodium salt solution of bisphenol A (BPA) per hour (9.12 kg of BPA per hour and 7.11 kg of 45% NaOH per hour), 120 kg of methylene chloride per hour, 11.9 kg of phosgene per hour and 15.2 kg of 45% sodium hydroxide solution per hour are continuously fed into a circulating pump reactor of the type shown in the accompanying diagram which has a volume of 19.4 l. The average time of stay in the reactor is 6 minutes and the reaction temperature 10°C. The pH of the reaction mixture is adjusted to 10.5. The reaction mixture leaving the reactor is transferred to a separator. The separated organic phase is washed with 20 l of water per hour. From this solution now washed free of electrolytes, the bischlorocarbonic acid ester is distilled under a high vacuum in a falling film evaporator after evaporation of the methylene chloride. The product boils at 216°C at a pressure of 2 Torr. The yield is 88 % of the theory, based on bisphenol A.

b. Polyurethane

A solution of 35.3 g (0.1 mol) of the bischlorocarbonic acid ester of 2,2-bis-(p-hydroxyphenyl)-propane obtained according to a) in 200 ml of methylene chloride is added dropwise with vigorous stirring over a period of about 1 hour at 15° to 35°C to a mixture of a solution of 25.4 g (0.1 mol) of 2,2-bis-(p-methylaminophenyl)-propane in 300 ml of methylene chloride and a solution of 8.8 g (0.22 mol) of sodium hydroxide in 80 ml of water, after the addition of 0.2 ml of triethylamine to the mixture as catalyst. The reaction mixture is left to react at the same temperature for 2 to 3 hours, i.e. until the organic solution of the resulting polyurethane has reached the desired viscosity. A clear, colourless product with a relative viscosity (methylene chloride 5 g/l solution) of 1.60 is obtained. It can be processed both from solution and from the melt to produce shaped articles such as fibres, films or foils. The freezing temperature determined by the DTA-method is 155°C and the decomposition temperature is above 360°C.

EXAMPLE 2

Tetrabromobisphenol A-bischlorocarbonic acid ester.

544 parts by weight of tetrabromobisphenol A dissolved in 2700 parts by weight of water, 178 parts by weight of 45% sodium hydroxide solution, 297 parts by weight of phosgene dissolved in 1400 parts by volume of methylene chloride and 457 parts by weight of 45% sodium hydroxide solution to maintain a pH of 9.5 are continuously fed into the circulating pump reactor used in example 1 and reacted at 15° to 20°C. The average time stay is 8.4 minutes.

To isolate the bischlorocarbonic acid ester, the organic phase is separated from the reacton mixture, washed free from electrolyte with water and freed from solvent by evaporation. Vacuum distillation at 280° to 285°C and a pressure of 2.2 Torr yields 529 parts by weight of tetrabromobisphenol A-bischlorocarbonic acid ester which has a melting point of 158°C. The yield is 79.5 % of the theory, based on tetrabromobisphenol A.

Example 3

Tetrachlorobisphenol A-bischlorocarbonic acid ester
7.3 kg of tetrachlorobisphenol A dissolved in 65.9 kg of 2.43 % aqueous sodium hydroxide solution, 7.92 kg of phosgene dissolved in 52.7 kg of chlorobenzene and 15.24 kg of 45% sodium hydroxide solution used to maintain a pH of 10.0 are continuously fed into the pump circulation reactor used in example 1 and reacted at 25°C. The average time of stay is 8.5 minutes.

The reaction mixture is transferred to a separating vessel. The separated organic phase is acidified with dilute phosphoric acid and then washed twice with water to free it from electrolytes. After evaporation of the major portion of chlorobenzene, tetrachlorobisphenol A-bischlorocarbonic acid ester crystallises at 10° to 15°C. The product is suction-filtered, washed with a small quantity of pure chlorobenzene and dried. The saponifiable chlorine content is 14.5 %, which corresponds to the theoretical value. The yield is found to be 81.3 % of the theory.

We claim:

1. A process for the continuous production of bisphenol bischlorocarbonic acid esters which comprises feeding a reaction mixture containing an aqueous dialkali metal salt solution of a hydroquinone or of an aromatic dihydroxy compound of the formula

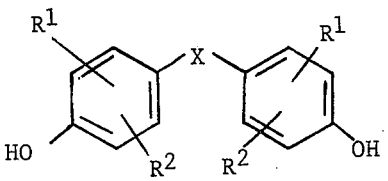

wherein X is alkylene or alkylidene having 1 to 6 carbon atoms, cycloalkylene or cycloalkylidene having 5 to 15 carbon atoms, O, S, $SO_2$ or

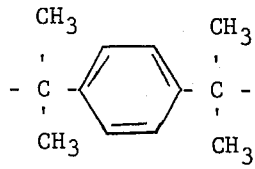

and $R^1$ and $R^2$, which may be the same or different, are alkyl having 1 to 4 carbon atoms, chlorine or bromine and containing 2.5–5.0 mol per mol of dihydroxy compound of phosgene dissolved in a water immiscible solvent for the bischlorocarbonic ester product into a pump circulation reactor including a delivery pump on the upstream side of the delivery pump, delaying an interval of at least 1 second after commencing said feeding and then introducing into said reaction mixture, as the sole acid neutralizing agent for acid byproduct, an alkali metal hydroxide solution at a rate to maintain the pH value of the reaction mixture between 9.0 and 12.0, maintaining the reaction mixture in said pump circulation reactor for a dwell time of up to 12 minutes and at a Reynolds number greater than 2,000, separating the organic phase from the resulting reaction mixture and recovering bisphenol bischlorocarbonic acid ester therefrom by distillation, crystallization or a combination thereof.

2. A process according to claim 1, wherein the dialkali metal salt solution used is the disodium or dipotassium salt solution of bisphenol A, tetrachlorobisphenol A, tetrabromobisphenol A and tetramethyl bisphenol A.

3. A process according to claim 1, wherein a 5–30 % by weight dialkali metal salt solution is used.

4. A process according to claim 1, wherein the phosgene is dissolved in an aromatic hydrocarbon or in a halogenated hydrocarbon.

5. A process according to claim 4, wherein the phosgene solvent used is methylene chloride, chloroform, 1,2-dichloroethane or chlorobenzene.

6. A process according to claim 1, wherein the reaction is carried out at 0° to 50°C.

* * * * *